(12) United States Patent
Bieberich (10) Patent No.: US 7,276,076 B2
(45) Date of Patent: Oct. 2, 2007

(54) PERIOPERATIVE WARMING DEVICE

(75) Inventor: Mark T. Bieberich, Minnetonka, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

(21) Appl. No.: 11/057,396

(22) Filed: Feb. 11, 2005

(65) Prior Publication Data

US 2006/0184215 A1   Aug. 17, 2006

Related U.S. Application Data

(63) Continuation-in-part of application No. 10/895,672, filed on Jul. 21, 2004, now abandoned.

(51) Int. Cl.
*A61F 7/00* (2006.01)

(52) U.S. Cl. .................. 607/108; 607/112; 607/104

(58) Field of Classification Search ............ 607/96, 607/104, 108, 112, 114
See application file for complete search history.

(56) References Cited

U.S. PATENT DOCUMENTS

| | | |
|---|---|---|
| 2,573,414 A | 10/1951 | Dunn |
| 2,826,758 A | 3/1958 | Kahn |
| 3,468,299 A | 9/1969 | D'Amato |
| 3,610,323 A | 10/1971 | Troyer |
| 3,855,635 A | 12/1974 | Ramirez |
| 3,911,499 A | 10/1975 | Benevento et al. |
| 3,950,789 A | 4/1976 | Konz et al. |
| 4,055,173 A | 10/1977 | Knab |
| 4,146,933 A | 4/1979 | Jenkins et al. |
| 4,369,528 A | 1/1983 | Vest et al. |
| 4,494,248 A | 1/1985 | Holder |
| 4,524,463 A | 6/1985 | Ogden |
| 4,558,468 A | 12/1985 | Landry et al. |
| 4,578,825 A | 4/1986 | Vote |
| 4,587,671 A | 5/1986 | Rodriguez, Jr. et al. |
| 4,651,727 A | 3/1987 | Howorth |
| 4,653,120 A | 3/1987 | Leaf |
| 4,787,101 A | 11/1988 | Feinberg |
| 4,914,752 A | 4/1990 | Hinson et al. |
| 4,964,282 A | 10/1990 | Wagner |
| 5,062,424 A | 11/1991 | Hooker |
| 5,255,390 A | 10/1993 | Gross et al. |
| 5,304,213 A | 4/1994 | Berke et al. ............ 607/104 |

(Continued)

FOREIGN PATENT DOCUMENTS

GB          475811          11/1937

(Continued)

OTHER PUBLICATIONS

PCT International Publication No. WO 03/086500 A2, Oct. 23, 2003 Arizant Healthcare Inc.*

(Continued)

*Primary Examiner*—Michael Peffley
(74) *Attorney, Agent, or Firm*—Incaplaw; Terrance A. Meador (57) ABSTRACT

A perioperative warming device includes a clinical garment having an inside surface supporting a convective apparatus with multiple stacked sections. One section of the convective apparatus is adapted to provide comfort warming by convection. Another section of the convective apparatus is adapted to provide therapeutic warming by convection.

12 Claims, 4 Drawing Sheets

U.S. PATENT DOCUMENTS

| | | | |
|---|---|---|---|
| 5,360,439 A | 11/1994 | Dickerhoff et al. | 607/104 |
| 5,367,710 A | 11/1994 | Karmin | |
| 5,411,541 A | 5/1995 | Bell et al. | |
| 5,443,488 A | 8/1995 | Namenye et al. | 607/104 |
| 5,572,742 A | 11/1996 | McFadden | |
| 5,575,006 A | 11/1996 | Wolfe | |
| 5,611,087 A | 3/1997 | Adkins | |
| 5,620,482 A | 4/1997 | Augustine et al. | 607/107 |
| 5,697,963 A * | 12/1997 | Augustine | 607/104 |
| 5,785,716 A | 7/1998 | Bayron | 607/108 |
| 5,891,187 A * | 4/1999 | Winthrop et al. | 607/96 |
| 5,970,519 A | 10/1999 | Weber | |
| 5,974,605 A | 11/1999 | Dickerhoff et al. | |
| 6,049,907 A | 4/2000 | Palomo | |
| 6,154,883 A | 12/2000 | Spann et al. | |
| 6,216,270 B1 | 4/2001 | Moquin et al. | |
| 6,235,659 B1 | 5/2001 | McAmish et al. | |
| 6,378,136 B2 | 4/2002 | Matsushita | |
| 6,484,321 B1 | 11/2002 | Shamam | |
| 6,511,501 B1 | 1/2003 | Augustine et al. | |
| 6,524,332 B1 | 2/2003 | Augustine et al. | 607/107 |
| 6,571,574 B1 | 6/2003 | Blackstone | |
| 6,596,019 B2 | 7/2003 | Turner et al. | 607/108 |
| 6,647,552 B1 | 11/2003 | Hogan | |
| 6,666,879 B2 | 12/2003 | Arnold et al. | 607/104 |
| 6,694,522 B1 | 2/2004 | Neal | |
| 6,792,622 B2 | 9/2004 | Graves | |
| 6,799,332 B2 | 10/2004 | Hatton | |
| 6,851,125 B2 | 2/2005 | Fujikawa et al. | 2/51 |
| 6,876,884 B2 | 4/2005 | Hansen et al. | |
| 7,001,416 B2 | 2/2006 | Augustine et al. | |
| 7,226,454 B2 | 6/2007 | Albrecht et al. | 607/104 |
| 2003/0195596 A1* | 10/2003 | Augustine et al. | 607/108 |
| 2005/0015127 A1 | 1/2005 | Augustine et al. | |
| 2005/0143796 A1 | 6/2005 | Augustine et al. | |
| 2006/0047332 A1 | 3/2006 | Malmberg et al. | 607/104 |
| 2006/0122671 A1 | 6/2006 | Albrecht et al. | |
| 2006/0122672 A1* | 6/2006 | Anderson | 607/104 |
| 2006/0147320 A1 | 7/2006 | Hansen et al. | |
| 2006/0184216 A1 | 8/2006 | Van Duren | |
| 2006/0184217 A1 | 8/2006 | Van Duren | |
| 2006/0184218 A1 | 8/2006 | Bieberich | |
| 2006/0259104 A1 | 11/2006 | Panser et al. | |

FOREIGN PATENT DOCUMENTS

| | | |
|---|---|---|
| GB | 1 462 003 | 1/1997 |
| SE | 525 415 | 2/2005 |
| WO | WO 97/14381 A1 | 4/1997 |
| WO | WO/98/48652 | 11/1998 |
| WO | WO/00/62726 | 10/2000 |
| WO | WO 03086500 | 10/2003 |
| WO | WO2003/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO2006/086587 A1 | 8/2006 |
| WO | WO 2007/047917 | 4/2007 |

OTHER PUBLICATIONS

PCT/US2005/025355, filed Jul. 18, 2005, International Search Report, PCT/ISA/210.

P.O. Fanger, Thermal Comfort: Analysis and Applications in Environmental Engineering, Danish Technical Press, 1970, pp. 5-67.

C.B. Mahony & J. Odom, Maintaining intraoperative normothermia: A meta-analysis of outcomes with costs. *AANA Journal*. Apr. 1999. v. 67, No. 2:155-164.

Porta-Chill—The Portable Air-Chiller—Brochure, http://www.portachil.com/, Dec. 3, 2002.

EPO Examination Report mailed Oct. 24, 2006, in EP03719690.4-1526, EP Regional Phase of PCT/US2003/11128 (published as WO/2003/086500).

International Search Report in PCT/US2006/041028, mailed Feb. 20, 2007.

Written Opinion of the International Search Authority (EPO) in PCT/US2006/041028, mailed Feb. 20, 2007.

International Search Report in PCT/US2006/004644, mailed Dec. 18, 2006.

Written Opinion of the International Search Authority (EPO) in PCT/US2006/004644, mailed Dec. 18, 2006.

* cited by examiner

PERIOPERATIVE WARMING DEVICE

RELATED APPLICATIONS

This application claims priority under 35 U.S.C. 120 as a continuation-in-part of U.S. patent application Ser. No. 10/895,672 filed Jul. 21, 2004 now abandoned, and contains subject matter related to the subject matter of the following patent applications, commonly owned herewith:

Patent Cooperation Treaty (PCT) Application No. PCT/US2003/11128, filed Apr. 10, 2003, entitled "Patient Comfort Apparatus and System", and published on Oct. 23, 2003 under Publication No. WO 2003/086500;

PCT Application No. PCT/US2005/025355, filed Jul. 18, 2005, entitled "Perioperative Warming Device", and published on Feb. 23, 2006 under Publication No. WO 2006/020170;

PCT Application No. PCT/US2005/043968, filed Dec. 6, 2005, entitled "Warming Device with Varied Permeability", and published on Jun. 15, 2006 under Publication No. WO 2006/062910;

PCT Application No. PCT/US2005/044214, filed Dec. 6, 2005, entitled "Warming Device", and published on Jun. 15, 2006 under Publication No. WO 2006/063027;

PCT Application No. PCT/US2006/004644, filed Feb. 9, 2006, entitled "Warming Device for Perioperative Use", and published on Aug. 17, 2006 under Publication No. WO2006/086587;

PCT Application No. PCT/US/2006/41028, filed Oct. 19, 2006, entitled "Multifunction Warming Device for Perioperative Use";

U.S. patent application Ser. No. 10/411,431, filed Apr. 10, 2003, entitled "Forced Air Warming Unit", now U.S. Pat. No. 6,876,884;

U.S. patent application Ser. No. 10/411,865, filed Apr. 10, 2003, entitled "Patient Comfort Apparatus and System", and published on Oct. 16, 2003 under Publication No. US 2003/0195596, now U.S. Pat. No. 7,001,416;

U.S. patent application Ser. No. 10/895,672, filed Jul. 21, 2004, entitled "Perioperative Warming Device", published on Jan. 20, 2005, under Publication No. US 2005/0015127, and now abandoned;

U.S. patent application Ser. No. 10/508,319, filed Sep. 20, 2004, entitled "Patient Comfort Apparatus and System", and published on Jun. 30, 2005 under Publication No. US 2005/0143796;

U.S. patent application Ser. No. 11/005,883, filed Dec. 7, 2004, entitled "Warming Device with Varied Permeability", and published on Jun. 8, 2006 under Publication No. US 2006/0122671;

U.S. patent application Ser. No. 11/006,491, filed Dec. 7, 2004, entitled "Warming Device", and published on Jun. 8, 2006 under Publication No. US 2006/0122672;

U.S. patent application Ser. No. 11/057,397, filed Feb. 11, 2005, entitled "Thermal Blanket for Warming the Limbs", and published on Aug. 17, 2006 under Publication No. US 2006/0184216;

U.S. patent application Ser. No. 11/057,403, filed Feb. 11, 2005, entitled "Warming Device for Perioperative Use", and published on Aug. 17, 2006 under Publication No. US 2006/0184217;

U.S. patent application Ser. No. 11/057,404, filed Feb. 11, 2005, entitled "Clinical Garment for Comfort Warming and Prewarming", and published on Aug. 17, 2006 under Publication No. US 2006/0184218;

U.S. patent application Ser. No. 11/260,706, filed Oct. 27, 2005, entitled "Patient Comfort Apparatus and System", and published on Mar. 9, 2006 under Publication No. US 2005/0052853;

U.S. patent application Ser. No. 11/363,136, filed Feb. 27, 2006, entitled "Forced Air Warming Unit", and published on Jul. 6, 2006 under Publication No. US 2006/0147320;

U.S. patent application Ser. No. 11/492,425, filed Jul. 25, 2006, entitled "Warming Device", and published on Nov. 16, 2006 under Publication No. US 2006/0259104;

U.S. patent application Ser. No. 11/583,432, filed Oct. 19, 2006, entitled "Multifunction Warming Device for Perioperative Use";

U.S. patent application Ser. No. 11/583,477, filed Oct. 19, 2006, entitled "Multifunction Warming Device with Provision for Being Secured";

U.S. patent application Ser. No. 11/583,480, filed Oct. 19, 2006, entitled "Multifunction Warming Device with Provision for Warming Hands";

U.S. patent application Ser. No. 11/583,481, filed Oct. 19, 2006, entitled "Multifunction Warming Device with an Upper Body Convective Apparatus"; and U.S. patent application Ser. No. 11/656,777, filed Jan. 23, 2007, entitled "Convective Warming Device with a Drape.

BACKGROUND OF THE INVENTION

A warming device for perioperative use includes a clinical garment and convective apparatus with multiple stacked sections supported on the inside of the garment.

Convective devices that transfer heat to a human body are known. For example, there are devices that receive a stream of warmed pressurized air, inflate in response to the pressurized air, distribute it within a pneumatic structure, and emit the warmed air onto a body to accomplish such objectives as increasing comfort, reducing shivering, and treating or preventing hypothermia. These devices are typically called "convective thermal blankets" or "covers". Arizant Healthcare Inc., the assignee of this application, makes and sells such thermal blankets under the BAIR HUGGER® brand. One such device is the Model 522 Upper Body Blanket.

Use of the term "convective" to denote the transfer of heat between a warming device and a body refers to the principal mode of heat transfer, it being understood that heat may at the same time be transferred between a convective warming device and a body by conduction and radiation, although not to the degree of convection.

A recent invention disclosed in the referenced PCT application adapts a clinical garment such as a robe or gown to receive a convective warming device in order to warm a person wearing the garment in a clinical setting for comfort and mobility of the person. Arizant Healthcare Inc., the assignee of this application, makes and sells such warming devices under the BAIR PAWS® brand. There is a need to further adapt such a combination for use perioperatively.

The term "perioperative" is defined in the *PDR Medical Dictionary*, Second Edition, (Medical Economics Company, 2000), as "around the time of operation." The perioperative period is characterized by a sequence including the time preceding an operation when a patient is being prepared for surgery ("the preoperative period"), followed by the time spent in surgery ("the intraoperative period"), and by the time following an operation when the patient is closely monitored for complications while recovering from the effects of anesthesia ("the postoperative period").

According to Mahoney et al. (Maintaining intraoperative normothermia: A meta-analysis of outcomes with costs. *AANA Journal*. 4/99;67,2:155-164.), therapeutic warming is employed during at least the intraoperative period in order to prevent or mitigate a constellation of effects that result from hypothermia. In fact, it is increasingly manifest that maintenance of normothermia perioperatively enhances the prospects for a quick, successful recovery from surgery. The effectiveness of therapeutic warming depends upon delivery of enough heat to a patient's body to raise the patient's core body temperature to, or maintain it within, a narrow range, typically near 37° C. This range is called "normothermic" and a body with a core temperature in this range is at "normothermia." Hypothermia occurs when the core body temperature falls below 36° C.; mild hypothermia occurs when core body temperature is in the range of 34° C. to 36° C. Therefore, "perioperative therapeutic warming" is warming therapy capable of being delivered during one or more of the perioperative periods for the prevention or treatment of hypothermia.

Therapeutic warming is contrasted with "comfort warming" which is intended to maintain or enhance a patient's sense of "thermal comfort". Of course, therapeutic warming may also comfort a patient by alleviating shivering or a feeling of being cold, but this is a secondary or ancillary effect. Thermal comfort is a subjective notion; however, the environmental conditions necessary to produce a sense of thermal comfort in a population of human beings are known and well tabulated. For example, Fanger (*Thermal Comfort: Analysis and Applications of Environmental Engineering*. Danish Technical press, Copenhagen, 1970) defines thermal comfort as "that condition of mind which expresses satisfaction with the thermal environment." Even when a patient is normothermic, less than ideal environmental conditions can result in acute feelings of discomfort. Under normothermic conditions, thermal comfort is largely determined with reference to skin temperature, not core body temperature. Comfort warming is warming applied to a patient to alleviate the patient's sense of thermal discomfort.

Therapeutic warming may be indicated during any one or more of the perioperative periods. For example, for a short operation in a surgery with no warming equipment available, a person may be warmed preoperatively in a preparation area to raise mean body temperature to a level higher than normal in order to store enough thermal energy to maintain normothermia, without heating, intraoperatively. After surgery, it may be necessary to apply therapeutic warming in a recovery area to raise the core temperature to normothermia and maintain it there for a period of time while anesthesia wears off. Alternatively, for a long surgery in an arena with heating equipment available, a person may be warmed for comfort before surgery and warmed therapeutically during and after surgery.

Both therapeutic warming and comfort warming may be provided by convective devices such as convective thermal blankets that receive and distribute warmed, pressurized air and then expel the distributed air through one or more surfaces toward a patient in order to prevent or treat hypothermia in the patient. An example of use of such a device for therapeutic warming is found in U.S. Pat. No. 6,524,332, "System and Method for Warming a Person to Prevent or Treat Hypothermia", commonly owned with this application. Comfort warming by convective means is described in the referenced U.S. Patent Application, and the referenced Publication No. WO 03/086500.

When delivered by convective devices, therapeutic warming is distinguished from comfort warming by intended effects and by the parameters of heat delivery that produce those effects. In this regard, a convective warming system typically includes a source of warmed pressurized air (also called a heater/blower unit, a forced air warming unit, a heater unit, etc.), a convective device such as a thermal blanket (which is, typically, inflatable), and a flexible conduit or air hose connecting the heater/blower unit with the thermal blanket. Use of such a system for a particular type of warming requires delivery of warmed air through a thermal blanket at parametric values that achieve a particular objective. The conditions by which a convective device such as a thermal blanket produces thermal comfort in normothermic individuals at steady state are significantly different from those necessary to treat hypothermia. Typically the conditions for thermal comfort are met in a system with a relatively low capacity heater/blower unit, while those in a therapeutic warming system are achieved with a relatively high capacity heater/blower unit. The different capacities have led to use of air hoses with different capacities, with those delivering air flow for thermal comfort typically having smaller diameters than those serving a therapeutic warming requirement. The result is a divergence of designs leading to installation of different air delivery infrastructures for therapeutic and comfort warming.

Health care cost is an issue of national importance. The cost of warming perioperatively is directly related to the number of perioperative periods in which a person is warmed; the cost increases when different warming apparatus are used in different periods to accomplish different goals. For example, when comfort and mobility are objectives of warming a person during the preoperative period and therapy is the objective of warming during one or more of the intraoperative and postoperative periods, it is presently necessary to use different warming configurations. Manifestly, if one warming device could be used or adapted to be used perioperatively, significant savings in thermal care could be realized.

SUMMARY

In one aspect, a perioperative warming device includes a clinical garment having an inside surface supporting a convective apparatus with multiple stacked sections. At least one section is adapted for comfort warming and at least another section is adapted for therapeutic warming.

In another aspect, a perioperative warming device includes a clinical garment and stacked convective apparatus in an integrated structure attached to the inside of the garment. At least one convective apparatus is adapted for comfort warming and at least another apparatus is adapted for therapeutic warming.

SPECIFICATION

A perioperative warming device is constituted of a clinical garment and a convective apparatus with multiple stacked sections supported on an inside surface of the garment. In this regard, a "clinical garment" is a garment that is typically used to temporarily clothe a patient in a clinical setting. Such garments include hospital gowns, robes, bibs and other equivalents. The clinical setting may be a medical or dental office or clinic, a hospital, or any facility or institution that provides medical or dental treatment to patients. The convective apparatus has multiple stacked sections, preferably two sections sharing a common member. The sections may be separate. Each section may receive and distribute at least one stream of warmed pressurized air in a pneumatic structure and circulate the air through a permeable member to thereby convectively warm a person wearing the clinical garment. One section is adapted for comfort warming by convection, the other for therapeutic warming by convection.

In one aspect, a warming device for perioperative use may be worn on a person where it receives a first stream of warmed pressurized air in one section of the convective apparatus, distributes the pressurized air within the one section, and emits the air through a permeable sheet of the one section to convectively warm the person's body for comfort. In another aspect, a warming device for perioperative use may be worn on a person where it receives a second stream of warmed pressurized air in the other section of the convective apparatus, distributes the pressurized air within the other section, and emits the air through a permeable sheet of the other section to convectively warm the person's body for therapy.

In the perioperative warming device illustrated and discussed below, each of the sections of the convective apparatus is inflatable. That is, the structure of each section, flaccid when not in use, tautens when receiving a stream of pressurized air.

Figure 1:
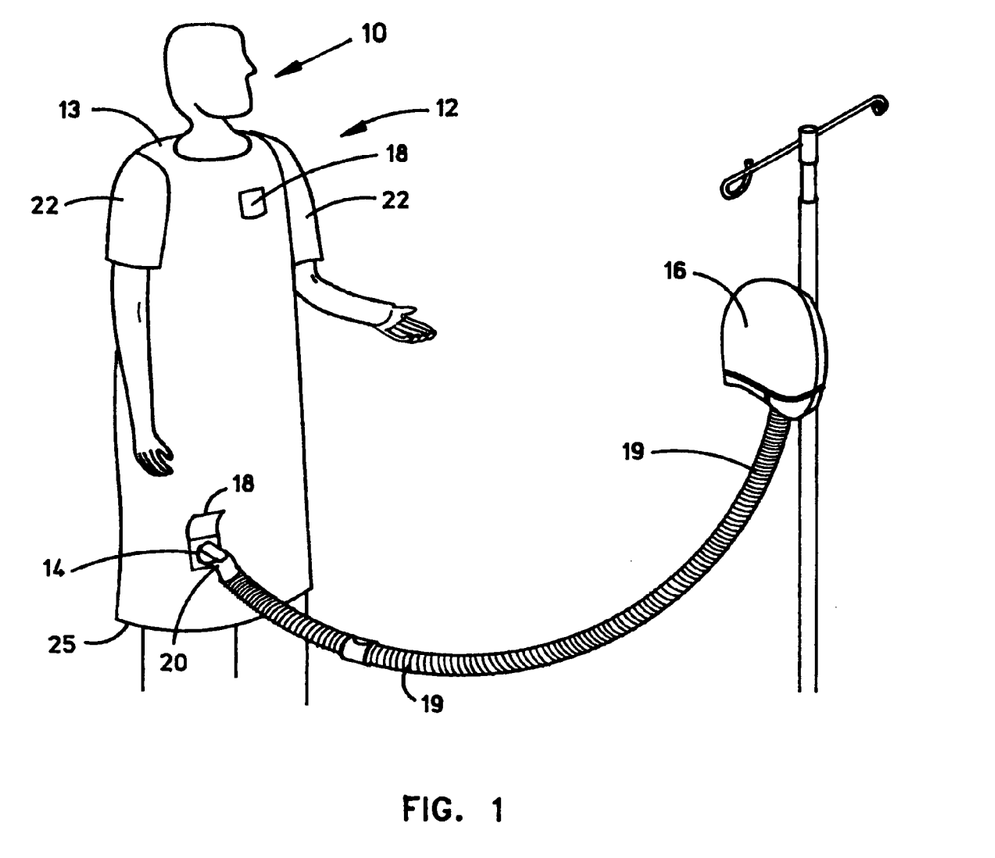
FIG. 1 is an illustration of a person wearing a perioperative warming device constituted of a clinical garment and a convective apparatus with multiple sections mounted to the inside of the garment.

Refer now to FIG. 1 in which a person 10 wearing a warming device 12 for perioperative use is shown. The perioperative warming device 12 is constituted of a clinical garment 13 and a convective apparatus with multiple stacked sections that is supported on an inside surface of the clinical garment 13. The convective apparatus has for example two separate sections that share a common member, each of which has at least one inlet port through which the section may receive warmed pressurized air from a heater/blower unit (not seen). Each inlet port is accessible through an aperture in the clinical garment 13. For example one inlet port 14 for one of the sections may be accessed through a lower flap 18 near the lower hem of the clinical garment 13. The lower flap is lifted and an air hose 19 with a nozzle 20 received in the inlet port 14 provides a pathway for a stream of warmed pressurized air to be conducted from a heater/blower unit 16 into the section through the inlet port 14. An inlet port of another section may be accessed through an upper flap 18 near the left sleeve of the clinical garment 13.

Convective apparatus such as thermal blankets have been specifically designed for particular uses. For example, a full body thermal blanket is adapted to lie upon the person and to extend longitudinally along the body of the person in order to cover substantially the person's entire body, from near the ankles or feet up to the neck. A lower body thermal blanket is adapted to lie upon the person and to extend longitudinally along the body of a person in order to cover the person's lower body, from near the ankles or feet up to the waist or pelvis of the person. An upper body thermal blanket has a bow-tie shape that is adapted to lie upon and extend transversely across the upper body of a person in order to cover the person's chest and extended arms. When fed a stream of warmed pressurized air, each of these thermal blankets inflates and distributes the air within itself. The pressurized air flows through apertures on a permeable surface of the thermal blanket which faces the person. These thermal blankets may have one, two, or more inlet ports through which an air hose provides warmed pressurized air from a heater/blower unit. The construction of thermal blankets is well understood. Examples of specific constructions are given in U.S. Pat. No. 5,620,482, U.S. Pat. No. 5,443,488, U.S. Pat. No. 5,360,439, and U.S. Pat. No. 5,304,213.

Most convective warming products are designed to provide a single mode of warming. Each of the thermal blankets described above is designed for therapeutic warming. The devices described in publication WO 03/086500 are designed for comfort warming. In contrast, the perioperative warming device described in this specification may provide either therapeutic warming or comfort warming, depending on the need. One section of the convective apparatus is constructed to provide comfort heating at steady state. Another section is constructed to provide therapeutic heating at steady state.

Figure 2:
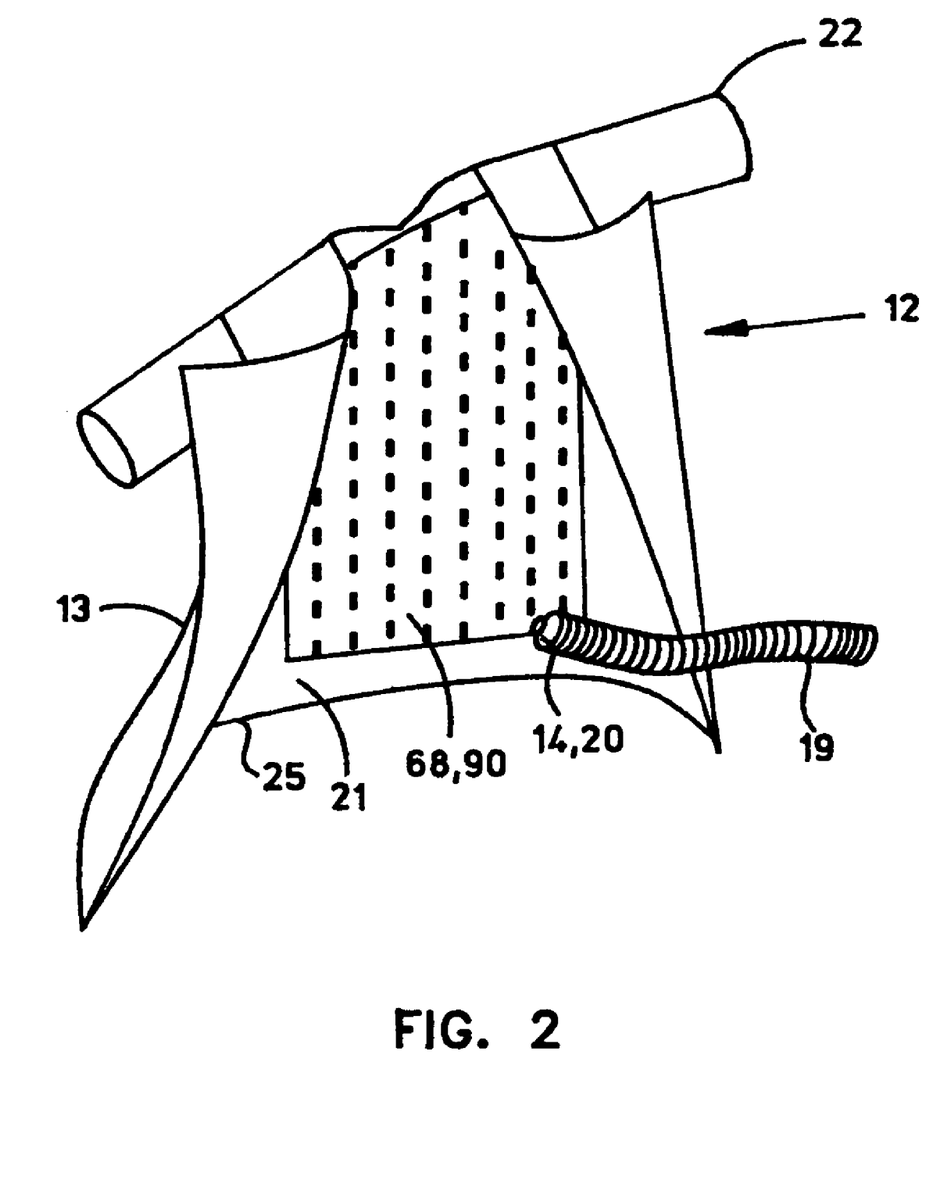
FIG. 2 illustrates a perspective view of the perioperative warming device looking into the clinical garment.

A convective apparatus with multiple sections is illustrated in FIG. 2 supported on the inside surface 21 of the clinical garment 13. In FIG. 2, the view is toward the inside of the clinical garment 13, looking toward a permeable surface (indicated by the hash lines) of at least one section of the convective apparatus 68, 90.

The convective apparatus 68, 90 has multiple sections. A "section" of the convective apparatus 68, 90 is a portion or division of the convective apparatus 68, 90 that may be inflated and operated separately from any other section of the convective apparatus 68, 90. For example, the convective apparatus 68, 90 has two sections. A first section may be inflated and operated separately from the second section, and the second section may be inflated and operated separately from the first section.

Figure 3A:
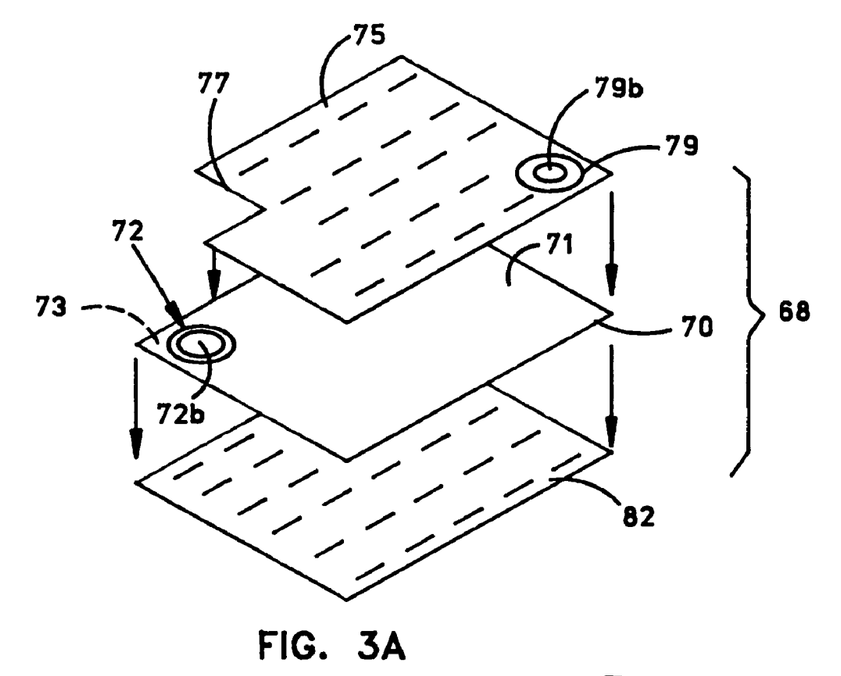
FIGS. 3A-3C illustrate assembly of a convective apparatus.

FIG. 3A illustrates assembly of a convective apparatus 68 by joining multiple sheets of material, with one of the sheets being common to both sections. An impermeable sheet 70 of material with a surface 71 has an inlet port 72 that opens through the sheet 70, near its periphery. A first permeable sheet 75 of material has a notch 77 formed near its periphery at a location corresponding to the location where the inlet port 72 is provided. The first permeable sheet 75 has another inlet port 79 provided at another location near its periphery; the inlet port 79 opens through the first permeable sheet 75. For example, the sheets 70 and 75 may have generally rectangular shapes with the inlet port 72 provided near a corner of the impermeable sheet 70 and the notch 77 provided at a corresponding corner of the first permeable sheet, and the inlet port 79 provided at a corner of the first permeable sheet 75 opposite the notch 77. The first permeable sheet 75 is brought to the surface 71 of the impermeable sheet 70 and the sheets 70 and 75 are joined by a seal ("the first peripheral seal") between the sheets along a trace that follows the peripheral outline of the first permeable sheet 75. The sheets 70 and 75 may be further joined by seals at stake points within the first peripheral seal. Thus a first section of the convective apparatus 68 is constituted of the impermeable sheet 70, the first permeable sheet 75, and the inlet port 79. The first section is an inflatable pneumatic structure with a permeable surface constituted of the outer surface of the first permeable sheet 75. As can be appreciated, with warmed pressurized air flowing into the first section through the inlet port 79, the first section will inflate and warmed pressurized air will circulate from within the section through the first permeable sheet 75. A second section is formed by bringing a second permeable sheet 82 to the surface of the impermeable sheet 70 opposite the surface 71 and joining the sheets 70 and 82 by a seal ("the second peripheral seal") between the sheets along a trace that follows the peripheral outlines of both sheets 70 and 82. The sheets 70 and 82 may be further joined by seals at stake points within the second peripheral seal. Thus a second section of the convective apparatus 68 is constituted of the impermeable sheet 70, the second permeable sheet 82, and the inlet port 72. The second section is an inflatable pneumatic structure with a permeable surface constituted of the outer surface of the second permeable sheet 82. As can be appreciated, with warmed pressurized air flowing into the second section through the inlet port 72, the second section will inflate and warmed pressurized air will circulate from within the section through the second permeable sheet 82. As can further be appreciated, the first and second sections may be said to be stacked in that the sections have an orderly arrangement one on top of the other when the convective apparatus 68 has the orientation shown in FIG. 3A. Further, the impermeable sheet constitutes a common element of the two sections.

In one aspect each of the inlet ports 72 and 79 may comprise a collar of relatively stiff material with an opening that is mounted to a sheet at an inlet port location. The opening in the collar of relatively stiff material coincides with an opening through the sheet on which it is mounted. Such inlet ports are taught for example in U.S. Pat. No. 6,666,879. Alternatively, each of the inlet ports may be a sleeve of material. The inlet port 79 of the first section has a smaller opening 79*b* than the opening 72*b* through the inlet port 72 of the second section. Consequently, the inlet port 79 accepts an air hose nozzle with a smaller diameter than the air hose nozzle diameter accepted by the inlet port 72. The smaller nozzle diameter signifies a comfort warming air supply with an air hose having a smaller diameter than the air hose of a therapeutic warming air supply. Further, the smaller air hose may be coupled to a heater blower unit with a smaller capacity than that of the heater blower unit of the therapeutic warming air supply. The smaller-diameter, smaller-capacity comfort warming air supply ensures that the first section operates in response to a heater/blower unit designed for comfort warming, while the larger-diameter, higher-capacity therapeutic air supply ensures that the second section in response to a heater/blower unit designed for therapeutic warming.

In another aspect, the permeabilities of the sheets 75 and 82 may differ. In this regard, the permeability of each sheet may be inherent in the material of which the sheet is made, or it may result from an assembly step in which apertures are formed in the sheet, or both. In any event, to further adapt the sheets 75 and 82 for their respective roles (comfort warming and therapeutic warming), the permeability of the sheet 82 may be greater than the permeability of the sheet 75. For example, the sheet 82 may have a permeability that is twice that of the sheet 75. According to another example the difference between the permeability of the sheet 75 and the permeability of the sheet 82 may result from manufacturing steps in which apertures are formed in the sheet 75 and in the sheet 82. In this example fewer apertures would be formed in the sheet 75 than in the sheet 82; for example sheet 75 would be manufactured to have no more than half the apertures of the sheet 82.

Figure 3B:
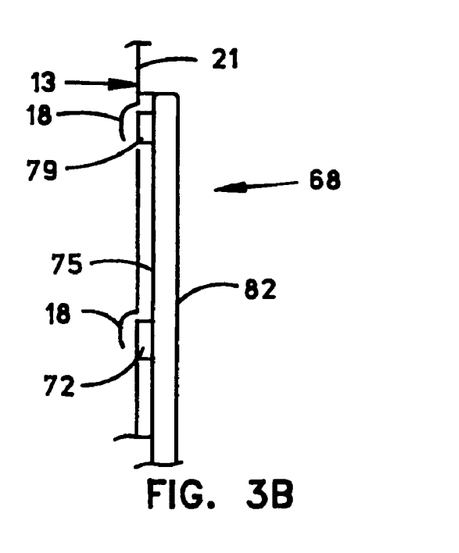
Figure 3C:
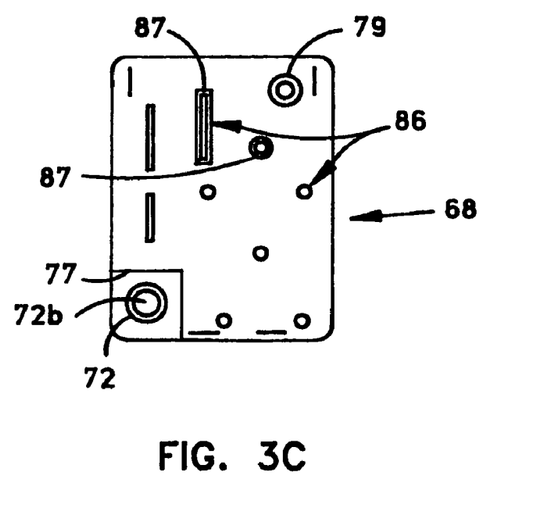

With reference to FIGS. 2, 3A and 3B, the convective apparatus 68 is supported in the clinical garment 13 on the inside surface 21 with the first permeable sheet 75, and thus the first section, facing the inside surface 21 and the second permeable sheet 82, and thus the second section, facing the interior of the clinical garment 13. Accordingly, when a stream of warmed pressurized air is provided through the inlet port 79 for comfort warming, the warmed pressurized air circulates through the first permeable sheet 75 toward the inside surface 21 of the clinical garment 13. When warmed pressurized air for therapeutic warming is provided through the inlet port 72, the warmed pressurized air circulates through the second permeable sheet 82 toward the interior of the clinical garment 13. In order to promote the circulation of warmed air for comfort warming to the interior of the clinical garment 13, one or more vents opening through the sheets 70, 75, and 82 may be provided as shown in FIG. 3C. Each such vent 86 must be completely surrounded around its periphery by a seal between the sheets 70 and 75 and a seal between the sheets 70 and 82. These seals are indicated in FIG. 3C by reference numeral 87.

Figure 4A:
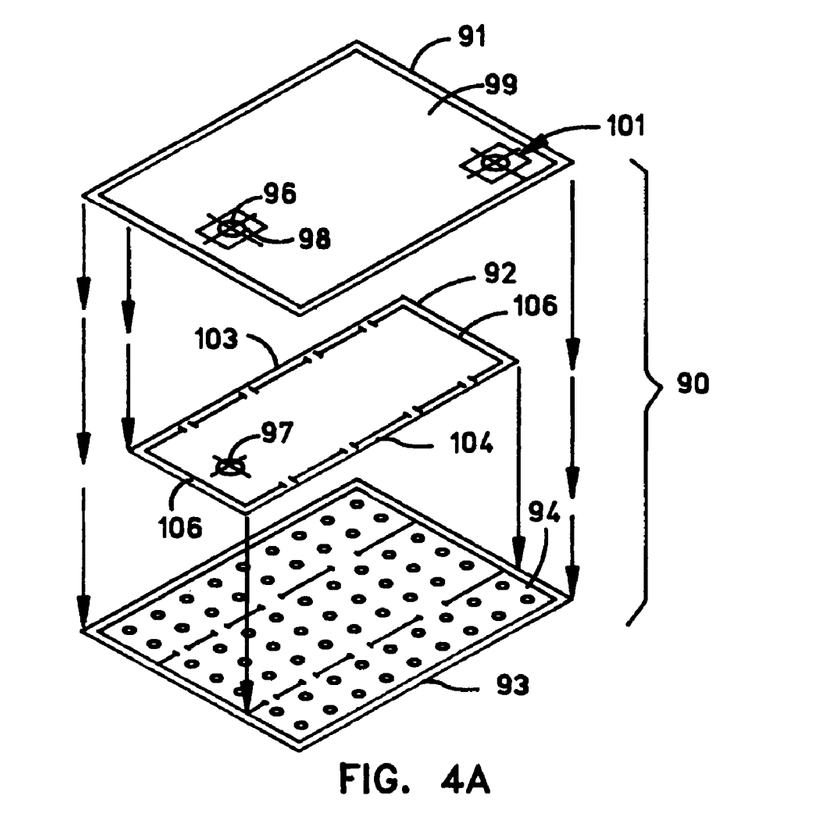
FIGS. 4A and 4B illustrate assembly of another convective apparatus.
Figure 4B:
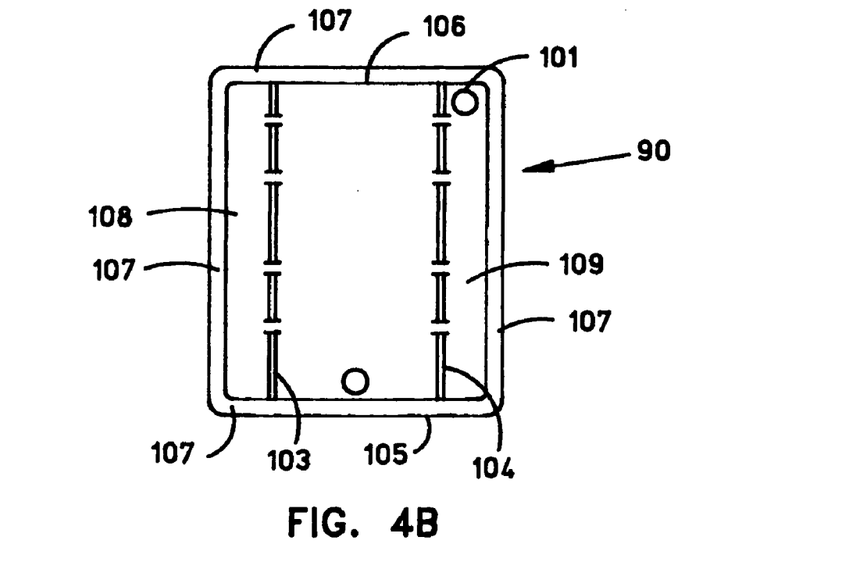

Another convective apparatus 90 is shown in FIGS. 4A and 4B. According to the exploded view shown in FIG. 4A, the convective apparatus 90 includes first and second impermeable sheets 91 and 92 of material and a permeable sheet 93 of material. For example, each of the sheets 91, 92, and 93 may have a generally rectangular shape, with the sheets 91 and 93 having substantially equal dimensions and the sheet 92 being substantially as long as, but narrower than, the sheets 91 and 93. Further, the sheet 92 is substantially centered between the long edges of the sheets 91 and 93. Aligned concentric openings 96 and 97 are provided in the first and second impermeable sheets 91 and 92, respectively. An inlet port 98 is mounted to the outside surface 99 of the first impermeable sheet 91. Another inlet port 101 is provided near a periphery of the first impermeable sheet 91, between an edge of the second impermeable sheet and the corresponding edge of the first impermeable sheet 92. The inlet ports 98 and 101 may have a structure as described above in connection with FIG. 3A. The second impermeable sheet 92 is brought to the surface 94 of the permeable sheet 93 and sealed thereto by interrupted lateral seals 103 and 104 and continuous end seals 105 and 106. The first impermeable sheet 91 is brought to the surface 94 of the permeable sheet 93, over the second impermeable sheet 92 and sealed to the surface 94 by a continuous seal 107 between the sheets 91 and 93 along their common periphery. Thus assembled, the second impermeable sheet 92 is sandwiched between the first impermeable sheet 91 and the permeable sheet 93. As can be seen in FIGS. 4A and 4B, this construction yields the convective apparatus 90 having a first section comprising the two permeable portions 108 and 109 of the permeable sheet 93 and a second section comprising the entirety of the permeable sheet 93. In this regard, when a stream of warmed pressurized air is introduced through the inlet port 101, the air flows into the first section and inflates the space between the sheets 91 and 93, and the pressure of the air in this space forces the second impermeable sheet 92 against and blocks the flow of air through the portion of the permeable sheet 93 between the portions 108 and 109. Consequently warmed pressurized air only circulates from the interior of the first section through the permeable portions 108 and 109. When a stream of warmed pressurized air is introduced through the inlet port 98, the air flows in the space between the sheets 92 and 93, through the interrupted lateral seals 103 and 104 and inflates the structure between the sheets 92 and 93 and the structure between the sheets 91 and 93. Air pressure in the structure between the second impermeable sheet 92 and the permeable sheet 93 keeps the second impermeable sheet 92 from contacting the permeable sheet 93. Consequently warmed pressurized air circulates from the interior of the second section through substantially the entirety of the permeable sheet 93.

The inlet port 101 of the first section has a smaller opening than the opening 72b through the inlet port 98 of the second section. Consequently, the inlet port 101 accepts an air hose nozzle with a smaller diameter than the air hose nozzle diameter accepted by the inlet port 98. The smaller nozzle diameter signifies a comfort warming air supply with an air hose having a smaller diameter than the air hose of a therapeutic warming air supply. Further, the smaller air hose may be coupled to a heater blower unit with a smaller capacity than that of the heater blower unit of the therapeutic warming air supply. The smaller-diameter, smaller-capacity comfort warming air supply ensures that the first section operates in response to a heater/blower unit designed for comfort warming, while the larger-diameter, higher-capacity therapeutic air supply ensures that the second section in response to a heater/blower unit designed for therapeutic warming.

As can be appreciated, the first and second sections may be said to be stacked in that the sections have an orderly arrangement one on top of the other when the convective apparatus 90 has the orientation shown in FIG. 4A. Further, the second impermeable sheet 92 and the permeable sheet 93 constitutes common elements of the two sections.

An impermeable sheet or a permeable sheet described above may be a single sheet or may have a laminate structure. A laminate sheet structure may include a layer of extruded synthetic material lined with a layer of non-woven material. If the permeable sheet has a laminate structure, holes or apertures are formed through both layers of the sheet to provide a permeable surface through which warmed pressurized air can be circulated. For sealing to form a convective apparatus, such laminate sheets may be oriented to have the extruded layers facing, and the seals may then be formed by a gluing process or by a heating or ultrasonic process acting through one of the layers of non-woven material. Once constructed, the convective apparatus may be attached to the inside surface of the clinical garment by known means and mechanisms.

In another construction of a convective apparatus a permeable sheet may comprise a sheet of permeable material in which the apertures are interstices in the material structure on the condition that the permeable material be capable of being sealed to an impermeable sheet of material.

In yet another alternative construction of a convective apparatus such as the convective apparatus 90, the clinical garment 13 may be constructed of a laminate sheet to which an apertured laminate sheet or a single sheet of permeable material, woven or non-woven, may be sealed.

Examples of non-woven material include any one or more of polyester, cotton, rayon, polypropylene, and wood pulp. Examples of extruded synthetic material include polypropylene, polyesters, and polyurethanes. Polyolefin plastics, including polyethylene, may provide the best results in terms of manufacturability since both woven and extruded materials may be made from them. Examples of attachment materials and mechanisms by which a convective apparatus as presented in FIGS. 3A and 4A can be attached to the inside surface 21 of the clinical garment 13 include two-sided adhesive, hook and loop, sewing, snaps, heat, ultrasonic, rivets, and any and all equivalents thereof.

The clinical garment 13 may be a standard gown, a modified gown or a special purpose gown. The gown may have a rear opening, a front opening or other suitable openings, such as a head opening in a poncho type gown. One type of gown shown in the figures has a rear opening. The clinical garment may be made of a woven cloth, such as cotton, or a non-woven such as spunbond-meltblown-spunbond material (SMS).

To secure the convective apparatus to a patient, a strip of double sided adhesive may be adhered along an edge of the device. During use of the perioperative warming device 12, a release liner may be removed from a surface of the strip facing the patient and adhered to the patient to prevent unintended movement of the convective apparatus 68, 90 during warming.

In use, a person is warmed perioperatively using a warming device constituted of a clinical garment and a dual-section convective apparatus supported on an inside surface of the clinical garment by dressing a person with the clinical garment during the preoperative period, coupling a first section of the convective apparatus to a source of warmed pressurized air for comfort warming, and convectively warming the person for comfort by way of the first section. To prepare for surgery, the first section is decoupled from the comfort warming source and the clinical garment is arranged to afford access to a surgical site. In preparation for surgery, the clinical garment may be left on the person, with its skirts rolled up to provide surgical access. Alternatively, the clinical garment may be removed to allow the convective apparatus to be positioned on the person to provide surgical access. In this latter case, the skirts, sleeves and other loose parts of the clinical garment may be rolled or folded onto the convective apparatus. In yet another alternative, if the convective apparatus is releasably attached to the inside surface of the clinical garment, the garment may be separated from the convective apparatus during surgery and reattached later postoperatively. During surgery, the convective apparatus may be secured to the person by means of the double sided adhesive and a second section of the convective apparatus may be coupled to a source of warmed pressurized air for therapeutic warming, and the person may be convectively warmed for therapy by way of the second section. Following surgery, the convective apparatus is detached from the person (but only if secured to the person for surgery), the convective is reattached to the clinical garment (but only if detached therefrom for surgery), the person is again dressed with the clinical garment and either warmed for comfort or warmed for therapy.

Manifestly, the descriptions and illustrations in this specification are presented for an understanding of how to make and use an exemplary perioperative warming device. The only limitations on the scope of protection afforded the inventive principles presented are in the following claims.

What is claimed is:

1. A perioperative warming device, comprising:
   a clinical garment with an inside surface; and
   a convective apparatus supported on the inside surface;
   the convective apparatus including first and second sheets of material sealed at a common periphery and a sheet of impermeable material disposed between the first and second sheets to define two separately inflatable sections, the first section adapted to provide comfort warming by convection and the second section adapted to provide therapeutic warming by convection.

2. The perioperative warming device of claim 1, wherein the first sheet of material is a permeable sheet of material, the first section includes a first portion of the permeable sheet of material, and the second section includes substantially the entire permeable sheet of material.

3. A perioperative warming device, comprising:
a clinical garment with an inside surface; and
a convective apparatus supported on the inside surface;
the convective apparatus including first and second separately inflatable sections sharing at least one common member, the first section adapted to provide comfort warming by convection and the second section adapted to provide therapeutic warming by convection;
wherein the convective apparatus further includes a permeable sheet of material, a first impermeable sheet of material substantially coextensive with the sheet of permeable material, a second impermeable sheet of material sandwiched between the first impermeable sheet of material and the permeable sheet of material, a continuous seal joining the first impermeable sheet of material to the permeable sheet of material at a common periphery, a pair of spaced apart intermittent seals joining the second impermeable sheet of material to the permeable sheet of material, a first inlet port opening through the first and second impermeable sheets of material to space between the second sheet of impermeable material and the sheet of permeable material, and a second inlet port opening through the first impermeable sheet of material to space between the first sheet of impermeable material and the sheet of permeable material between one of the intermittent seals and the continuous seal.

4. The perioperative warming device of claim 3, wherein the first section includes the second inlet port and at least one portion of the sheet of permeable material between the first sheet of impermeable material and the sheet of permeable material between one of the intermittent seals and the continuous seal.

5. The perioperative warming device of claim 3, wherein the first section includes the second inlet port and two portions of the sheet of permeable material, a first portion between the first sheet of impermeable material and the sheet of permeable material between a first of the intermittent seals and the continuous seal, and the second portion between the first sheet of impermeable material and the sheet of permeable material between a second of the intermittent seals and the continuous seal.

6. The perioperative warming device of claim 3, wherein the second section includes the first inlet port and substantially the entire sheet of permeable material.

7. A perioperative warming device, comprising:
a clinical garment with an inside surface; and
a convective apparatus supported on the inside surface;
the convective apparatus including:
 a permeable sheet of material;
 a first impermeable sheet of material substantially coextensive with the sheet of permeable material;
 a second impermeable sheet of material sandwiched between the first impermeable sheet of material and the permeable sheet of material;
 a continuous seal joining the first impermeable sheet of material to the permeable sheet of material at a common periphery;
 a pair of spaced apart intermittent seals joining the second impermeable sheet of material to the permeable sheet of material;
 a first inlet port opening through the first and second impermeable sheets of material to space between the second sheet of impermeable material and the sheet of permeable material; and
 a second inlet port opening through the first impermeable sheet of material to space between the first sheet of impermeable material and the sheet of permeable material between one of the intermittent seals and the continuous seal.

8. The perioperative warming device of claim 7, wherein the first and second inlet ports each include a collar of material with an opening.

9. The perioperative warming device of claim 8, wherein the opening in the first inlet port is larger than the opening in the second inlet port.

10. The perioperative warming device of claim 8, wherein the openings in the first and second inlet ports are for accepting air hose nozzles.

11. The perioperative warming device of claim 10, wherein the opening in the first inlet port accepts an air hose nozzle with a larger diameter than the opening in the second inlet port.

12. The perioperative warming device of claim 7, the first and second inlet ports each include a sleeve of material.

* * * * *